US00PP31578P3

(12) United States Plant Patent
Pierron-Darbonne

(10) Patent No.: US PP31,578 P3
(45) Date of Patent: Mar. 24, 2020

(54) RASPBERRY PLANT NAMED 'PLAPINK 0740'

(50) Latin Name: ***Rubus idaeus* L.**
Varietal Denomination: Plapink 0740

(71) Applicant: Plantas de Navarra, S.A. Sociedad Unipersonal, Navarra (ES)

(72) Inventor: Alexandre Pierron-Darbonne, Pamplona (ES)

(73) Assignee: Plantas de Navarra, S.A. Sociedad Unipersonal, Valtierra, Navarra (ES)

( * ) Notice: Subject to any disclaimer, the term of this patent is extended or adjusted under 35 U.S.C. 154(b) by 0 days.

(21) Appl. No.: 15/998,289

(22) Filed: Aug. 1, 2018

(65) Prior Publication Data

US 2019/0045685 P1 Feb. 7, 2019

(30) Foreign Application Priority Data

Aug. 3, 2017 (QZ) ..... PBR 2017/1920

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/0887; A01H 5/08; A01H 5/0216; A01H 5/0831; A01H 6/7499; A01H 6/74
See application file for complete search history.

(56) References Cited

PUBLICATIONS

Finn et al. Raspberry Cultivars for the Pacific Northwest, A Pacific Northwest Extension Publication PNW 655, 2014, retrieved on Jul. 9, 2019, retrieved from the Internet at https://catalog.extension.oregonstate.edu/sites/catalog/files/project/pdf/pnw655.pdf, pp. 1-11. (Year: 2014).*

* cited by examiner

*Primary Examiner* — June Hwu
(74) *Attorney, Agent, or Firm* — Knobbe, Martens, Olson & Bear, LLP

(57) ABSTRACT

Described is a new and distinct raspberry variety with varietal denomination 'Plapink 0740', characterized by a combination of traits which include, but are not limited to, sparse to medium spines density and very abundant production of orange to light red colored, conical shaped, and medium to large fruit size. 'Plapink 0740' is a self-fertile variety.

20 Drawing Sheets

Botanical classification: *Rubus idaeus* L.

Variety denomination: The new plant has the varietal denomination 'Plapink 0740'.

CROSS-REFERENCE TO RELATED APPLICATIONS

This application claims the benefit of European Community Plant Variety Office Application No. 2017/1920, for a raspberry variety named 'Plapink 0740,' filed on Aug. 3, 2017, the entirety of which is incorporated by reference herein.

BACKGROUND

Disclosed herein is a new and distinct raspberry variety. The varietal denomination of the new variety is 'Plapink 0740'. The new variety was designated by the breeder as '07.09R.40'. The new variety of raspberry was created in a breeding program by crossing two parents; in particular, by crossing as seed parent an undistributed raspberry parent designated '06.09R.84' (unpatented) and as pollen parent an undistributed raspberry parent designated '06.13R.46' (unpatented). Female and male are selections from breeder's program of Planasa. Both parental varieties are property and have not been commercialized.

The resulting seedling of the new variety was grown and asexually propagated by root cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Huelva, Spain, where the observations on primocane production were made, is between the end of June and the end of May of the following year.

SUMMARY

The present invention relates to a new and distinct raspberry variety. The varietal denomination of the new variety is 'Plapink 0740', that produces and maintains a strong vigorous plant with consistent fruit production from the middle of October through January on primocanes and in the ensuing year from the middle of April and ending in May.

Among the characteristics which appear to distinguish the new variety from other varieties are a combination of traits which include a sparse to medium spine density and very abundant production of orange to light red colored (RHS red group color near 42 B to 42 A), conical shaped, and medium to large fruit size.

COMPARISON TO THE PARENTS

Neither the seed parental cultivar, '06.09R84,' nor the pollen parent cultivar, '06.13R.46', has any patent or application for Plant Patent Rights in any country on the world.

Both the seed and pollen parentals were obtained by the Applicant. They are selections from breeder's program of the Applicant. They are property of the Applicant. The Applicant maintains them in their nurseries, and both parental cultivars have never been commercialized.

The new variety is distinguished therefrom its parents by the following characteristics possessed by 'Plapink 0740' which are different than, or not possessed by, the seed parent designated '06.09R.84' (unpatented) and the pollen parent designated '06.13R.46' (unpatented).

Predominant number of leaflets in leaf of seed parent '06.09R.84' (unpatented) is five, whereas for 'Plapink 0740' is three.

Seed parent '06.09R.84' (unpatented) and pollen parent '06.13R.46' (unpatented) show a smaller size fruit than the fruit of the new variety 'Plapink 0740' is medium to large.

Seed parent '06.09R.84' (unpatented) and pollen parent '06.13R.46' (unpatented) show a broad conical fruit shape compared to the fruit shape of the new variety 'Plapink 0740,' which is conical.

In seed parent '06.09R.84' (unpatented) the plug is small and rounded shaped, whereas the new variety 'Plapink 0740' presents a large plug and lengthened shape.

In pollen parent '06.13R.46' (unpatented) the plug is medium and pyramid shaped, whereas the new variety 'Plapink 0740' presents a large plug and lengthened shape.

COMPARISON TO CLOSEST VARIETY

The new variety 'Plapink 0740' is closest to the variety 'Adelita' (patented in U.S. Plant Pat. No. 25,245) and to the variety 'Lupita' (patented in U.S. Plant Pat. No. 25,171), but is distinguished therefrom by the following characteristics possessed by 'Plapink 0740' which are different than, or not possessed by, 'Adelita' (U.S. Plant Pat. No. 25,245) or 'Lupita' (U.S. Plant Pat. No. 25,171).

Leaf green color of upper side in 'Adelita' (U.S. Plant Pat. No. 25,245) is a green color (RHS green group near 138 A to 137A), whereas in 'Plapink 0740' it is a green color (RHS green group near 139 C to 139 B).

Length of terminal leaflet in 'Adelita' (U.S. Plant Pat. No. 25,245) is long to very long, whereas in 'Plapink 0740' is medium.

'Adelita' (U.S. Plant Pat. No. 25,245) shows a red color fruit (RHS red group near 47 A to 46 A), whereas 'Plapink 0740' shows a fruit red color fruit (RHS red group near 42 B to 42 A).

Fruit of 'Adelita' (U.S. Plant Pat. No. 25,245) shows a large ratio length/width, whereas fruit of 'Plaplink 0740' shows a medium to large ratio length/width.

Time of beginning of flowering on currents season's cane of 'Adelita' (U.S. Plant Pat. No. 25,245) is early to medium, whereas time of beginning of flowering on currents season's cane of 'Plapink 0740' is medium to late.

Time of beginning of fruit ripening on current year's cane of 'Adelita' (U.S. Plant Pat. No. 25,245) is early; whereas time of beginning of fruit ripening on current year's cane of 'Plapink 0740' is medium.

Time of beginning of flowering on currents season's cane of 'Lupita' (U.S. Plant Pat. No. 25,171) is medium, whereas time of beginning of flowering on currents season's cane of 'Plapink 0740' is medium to late.

'Lupita' (U.S. Plant Pat. No. 25,171) shows a medium density of spines; whereas 'Plapink 0740' shows a sparse to medium density.

'Lupita' (U.S. Plant Pat. No. 25,171) shows a broad conical fruit shape, whereas 'Plapink 0740' shows a conical fruit shape.

'Lupita' (U.S. Plant Pat. No. 25,171) shows a red color fruit (RHS red group near 45 D to 46 B), whereas 'Plapink 0740' shows a fruit red color fruit (RHS red group near 42 B to 42 A).

Time of beginning of fruit ripening on current year's cane of 'Lupita' (U.S. Plant Pat. No. 25,171) is early to medium; whereas time of beginning of fruit ripening on current year's cane of 'Plapink 0740' is medium.

Differences in the leaf color upperside of 'Plapink 0740' (designated 07.09R.40) and 'Adelita' (U.S. Plant Pat. No. 25,245) and differences in the length of the terminal leaflet of 'Plapink 0740' (designated 07.09R.40) and 'Adelita' (U.S. Plant Pat. No. 25,245) are show in FIG. 3 and FIG. 17.

Differences in fruit color and ratio length/width of fruits of 'Plapink 0740' (designated 07.09R.40) and 'Adelita' (U.S. Plant Pat. No. 25,245) are shown in FIG. 15 and FIG. 16.

Differences in spines density of 'Plapink 0740' (designated 07.09R.40) and 'Lupita' (U.S. Plant Pat. No. 25,171) are shown in FIG. 8 and FIG. 18.

Differences in fruit color and shape fruit of 'Plapink 0740' (designated 07.09R.40) and 'Lupita' (U.S. Plant Pat. No. 25,171) are shown in FIG. 19 and FIG. 20.

These differences are maintained during the harvest season.

BRIEF DESCRIPTION OF THE ILUSTRATIONS

The accompanying photographs show typical specimens of the new variety, designated 07.09R.40 in the illustrations, including fruit, foliage and flower, in color as nearly true as it is reasonably possible to make in color illustrations of this character.

The plants depicted in the drawings were planted June 21 in the farm of La Mogalla in Cartaya (Huelva), Spain, about 7° W, 37° N, 45 feet elevation.

Drawings were taken December (about December 10 and December 30,): minimum temperate about 5° to 6° Centigrade, maximun temperate about 18 to 22° Centigrade.

FIG. 1 and FIG. 2 shows several plants of the new variety (designated 07.09R.40) which exhibit a semi-upright habit plant with several red colored and conical shape fruits.

FIG. 3 and FIG. 4 show the upperside and the underside, respectively, of a complete leave of the new variety (designated 07.09R.40). It can be seen that the leaf color of upper side of the new variety (designated 07.09R.40) is a green color (RHS green group near 139 C to 139 B) and the leaf color of underside of the new variety (designated 07.09R.40) is RHS green group color (near 133 C to 133 B).

FIG. 5 and FIG. 6 show the upperside and the underside, respectively, of terminal leaflet of the new variety (designated 07.09R.40). In it can be seen that the leaf color of upper side of the new variety (designated 07.09R.40) is a green color (RHS green group near 139 C to 139 B) and the leaf color of underside of the new variety (designated 07.09R.40) is RHS green group color (near 133 C to 133 B) and length of terminal leaflet in the new variety (designated 07.09R.40) is medium.

Figure 1:
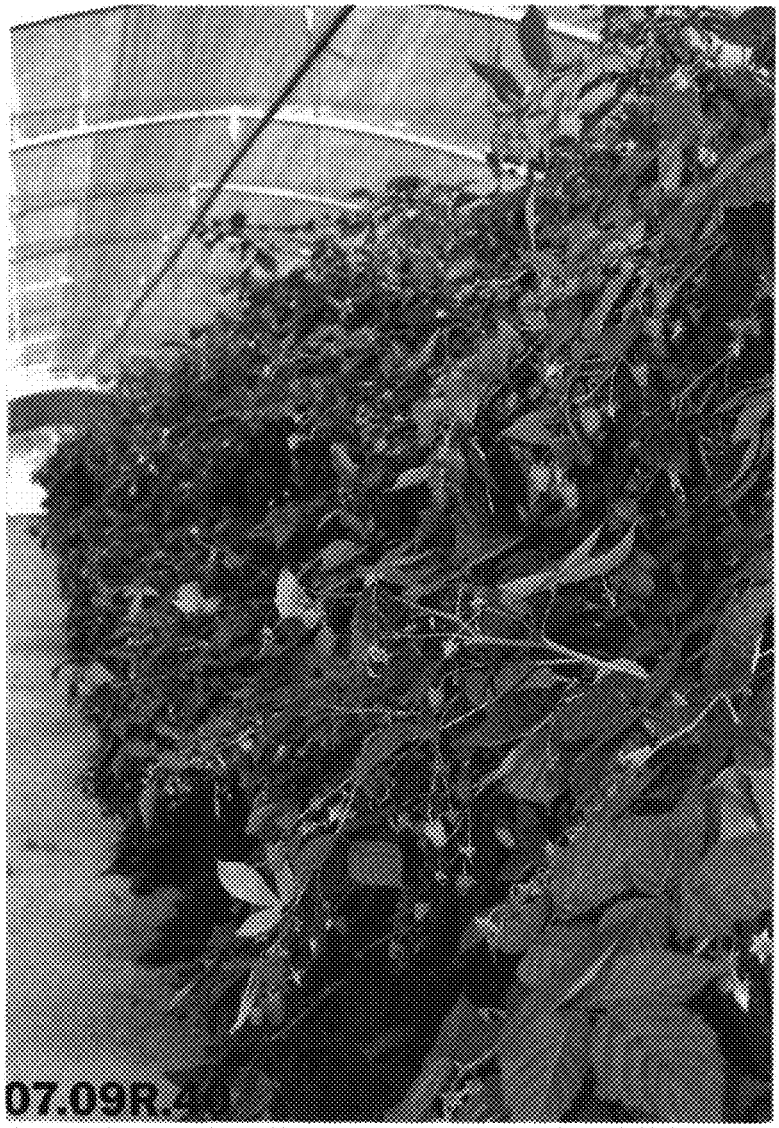
Figure 2:
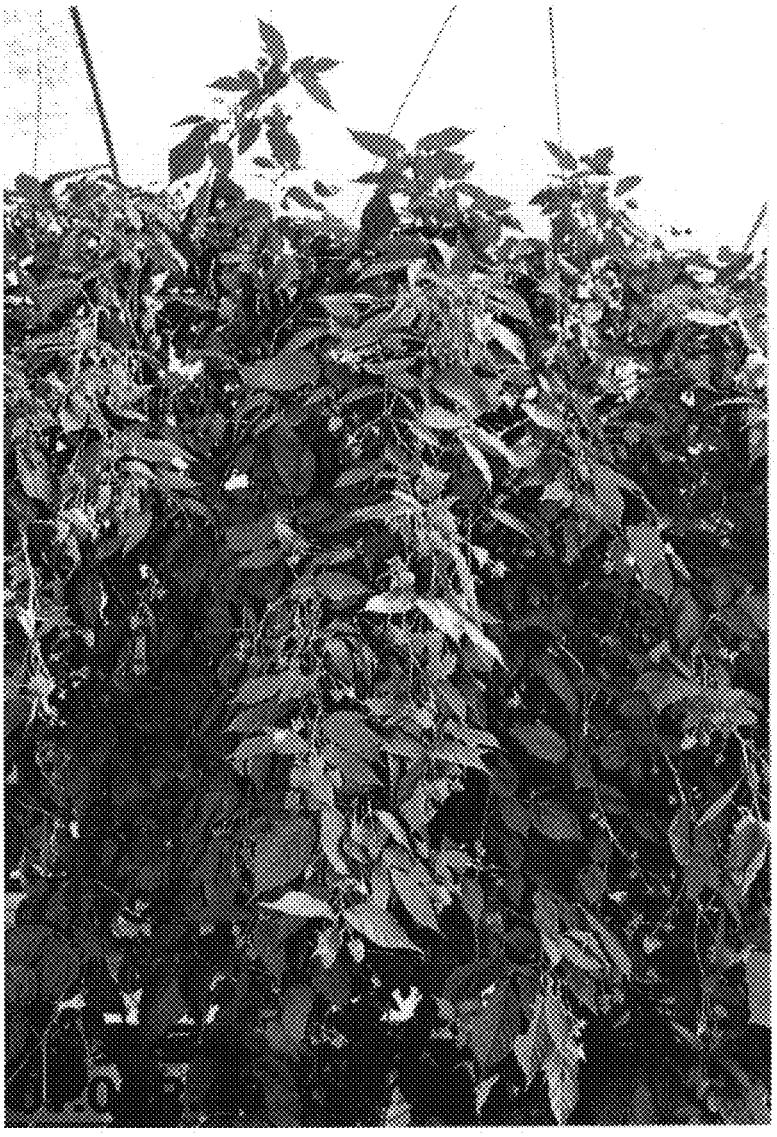
Figure 3:
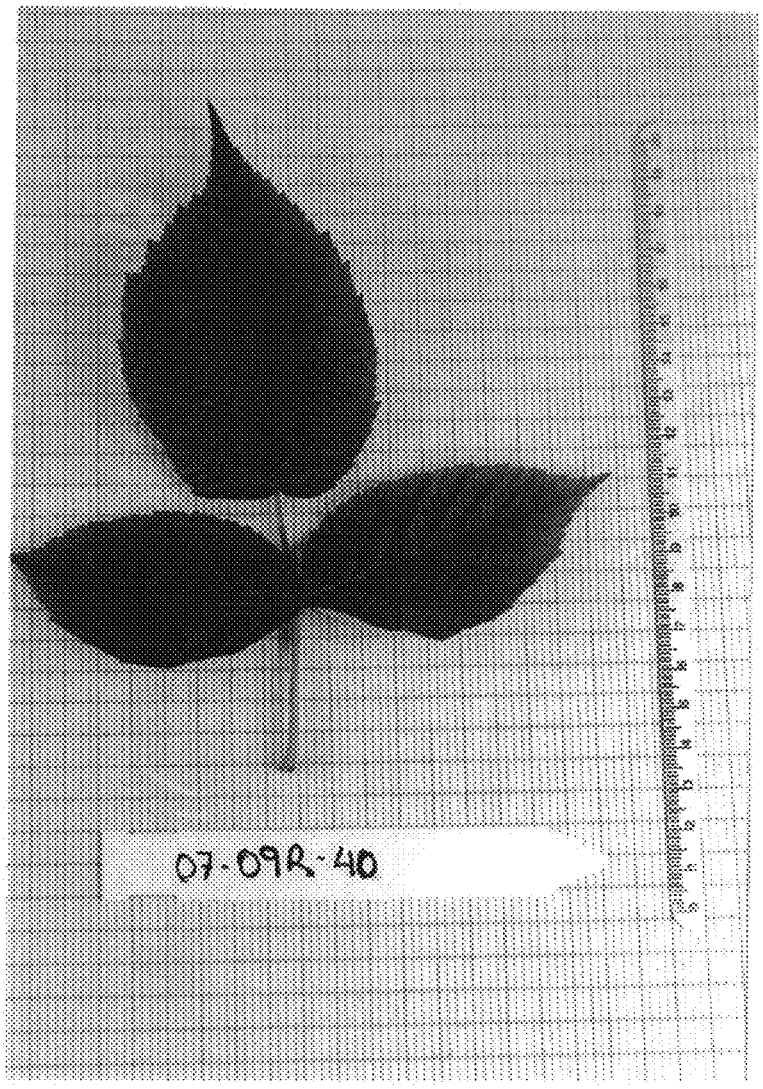
Figure 4:
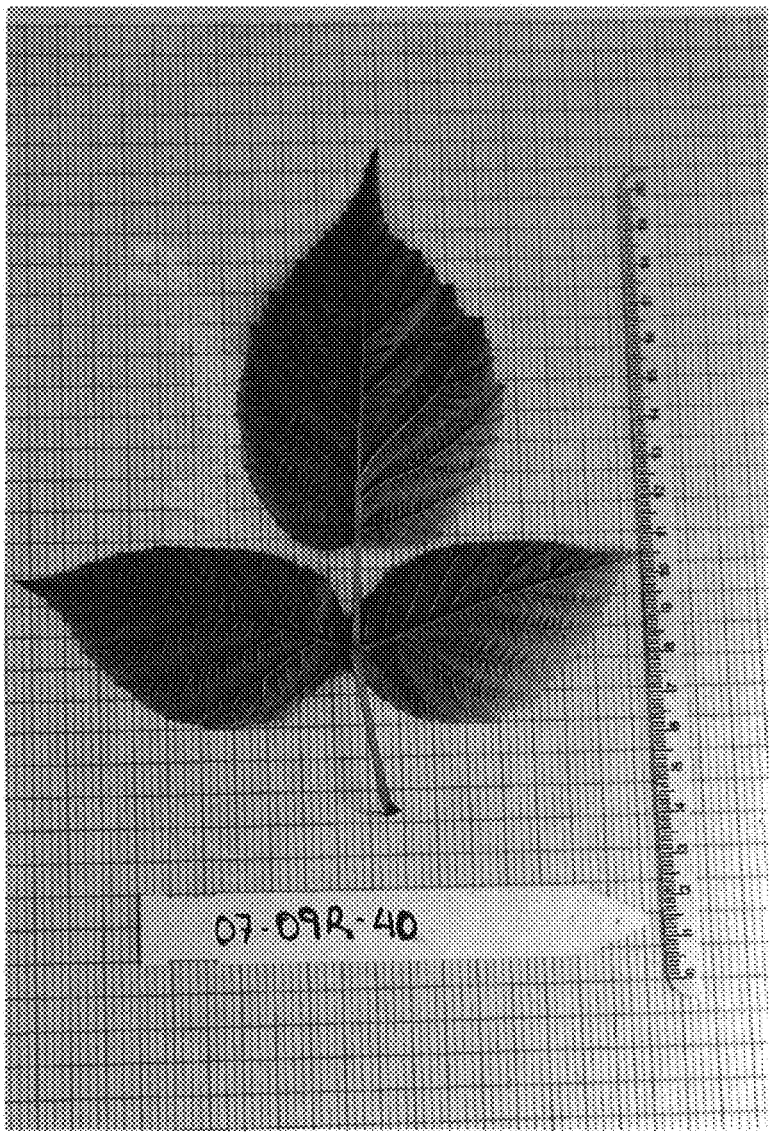
Figure 5:
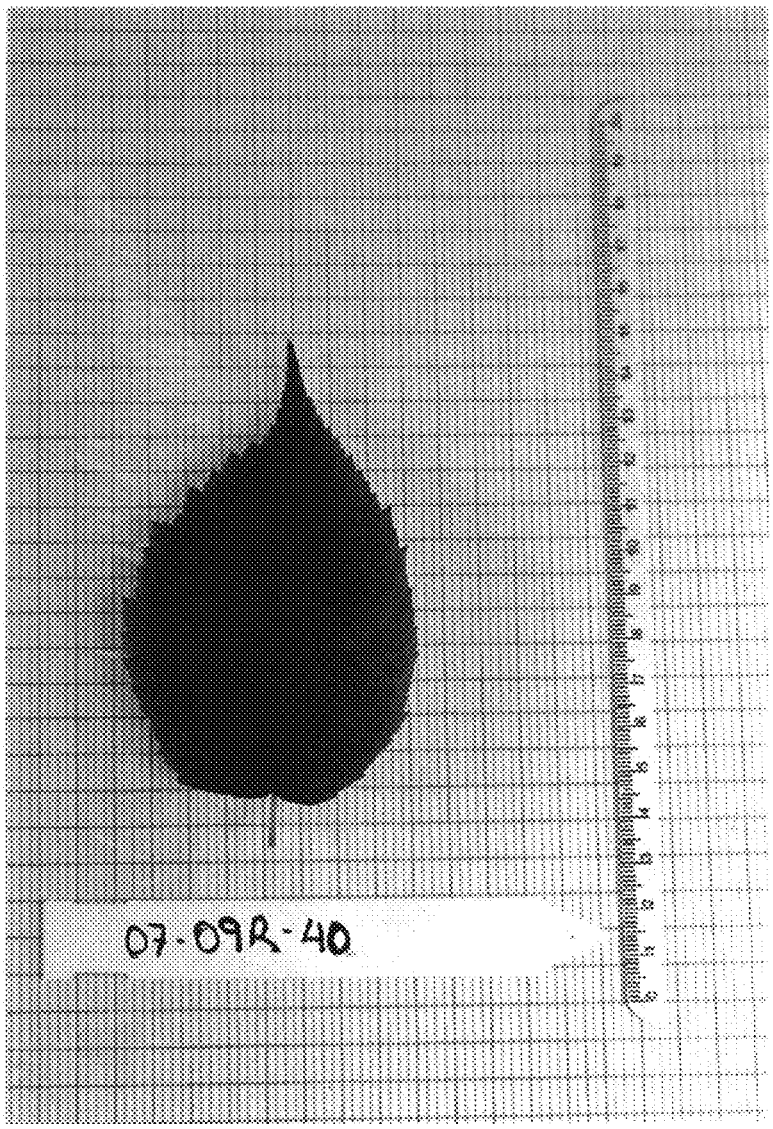
Figure 6:
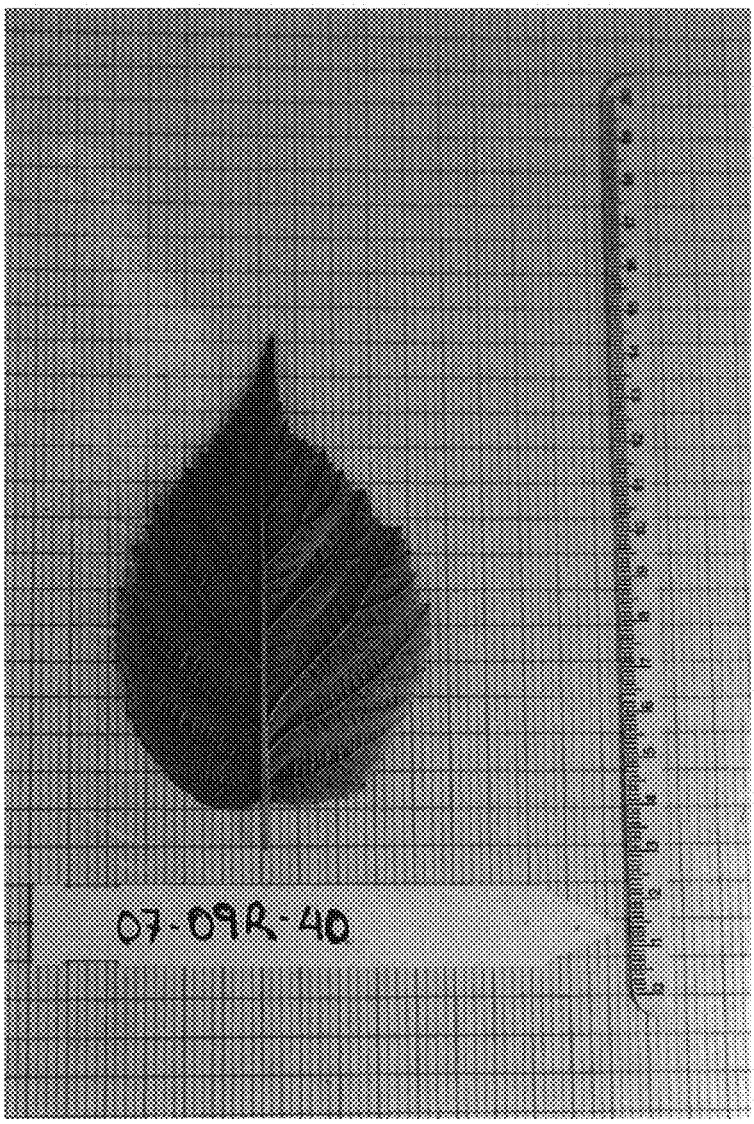
Figure 7:
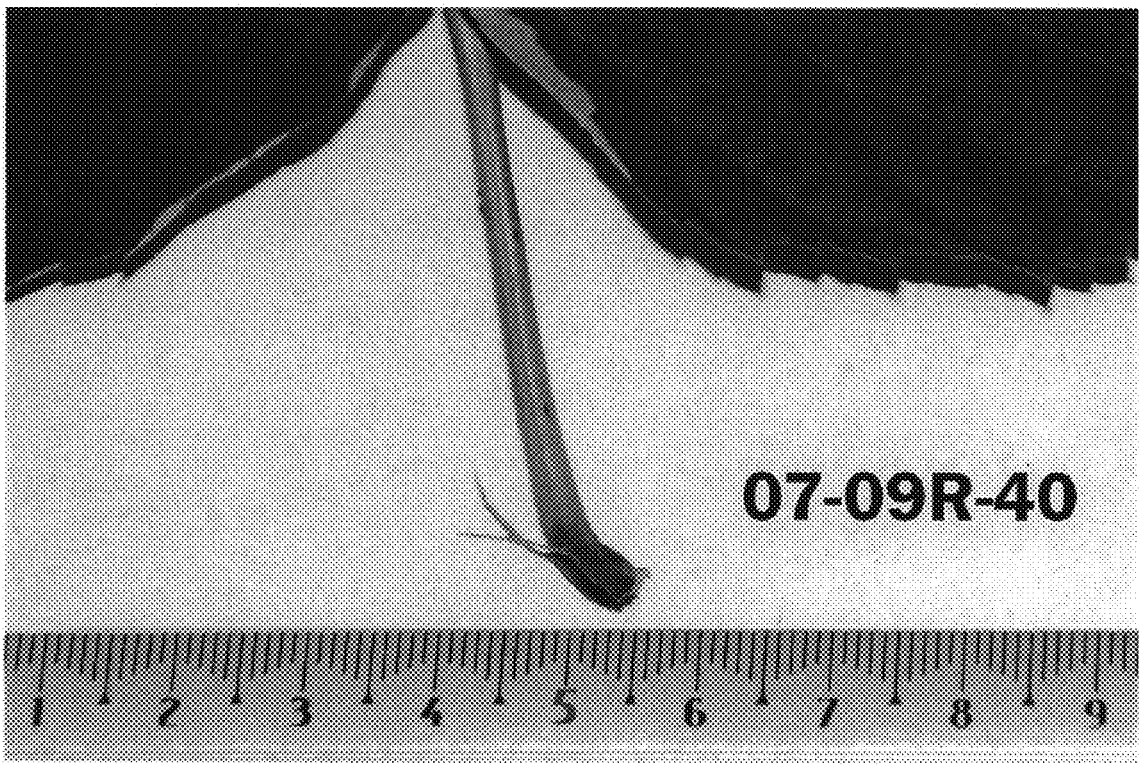
FIG. 7 shows the petiole of the new variety (designated 07.09R.40) without or very few spines and two erect and very narrow stipules.
Figure 8:
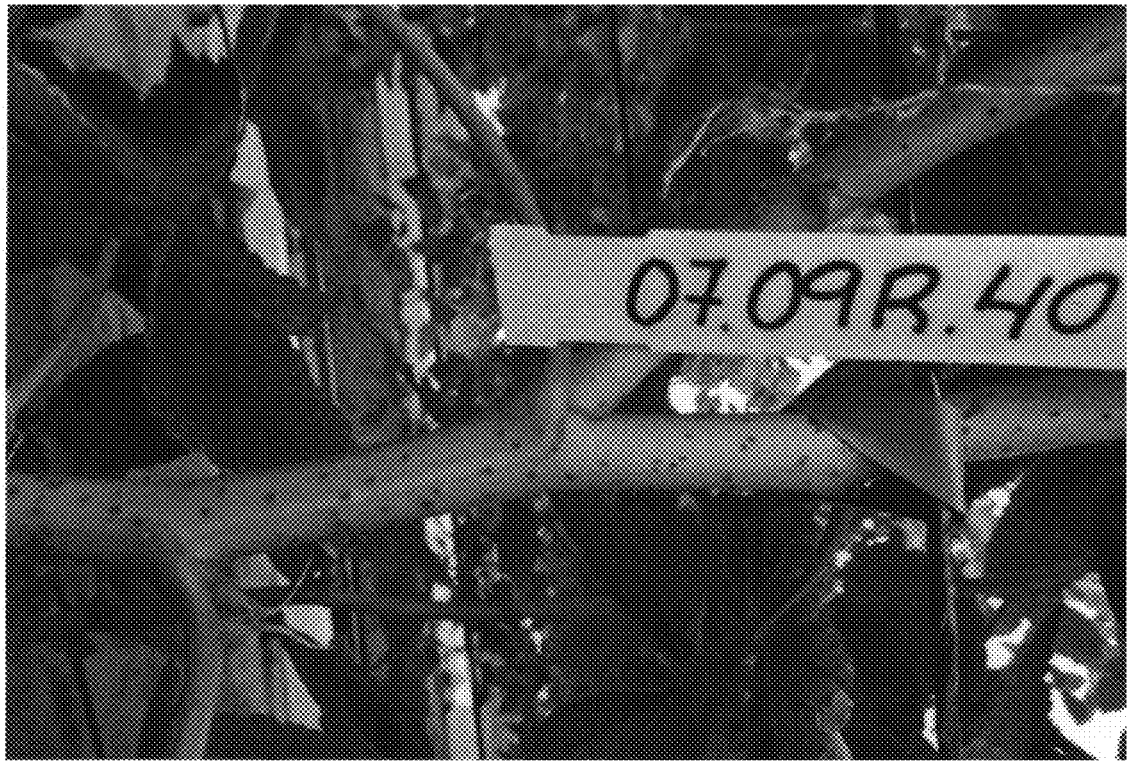
FIG. 8 shows the color cane of the new variety (designated 07.09R.40) RHS yellow green group (near 144 C to 144 B). It can be seen that the spines density is sparse to medium.
Figure 9:
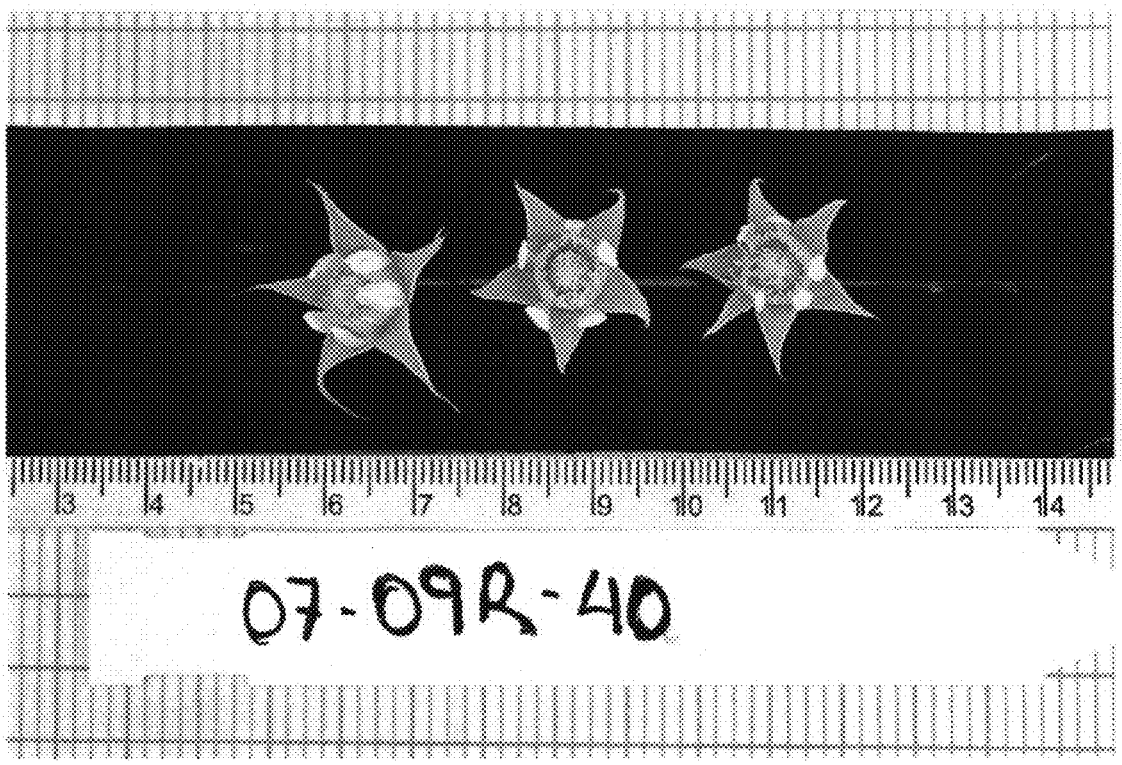
FIG. 9 shows typical flowers of the new variety (designated 07.09R.40).
Figure 10:
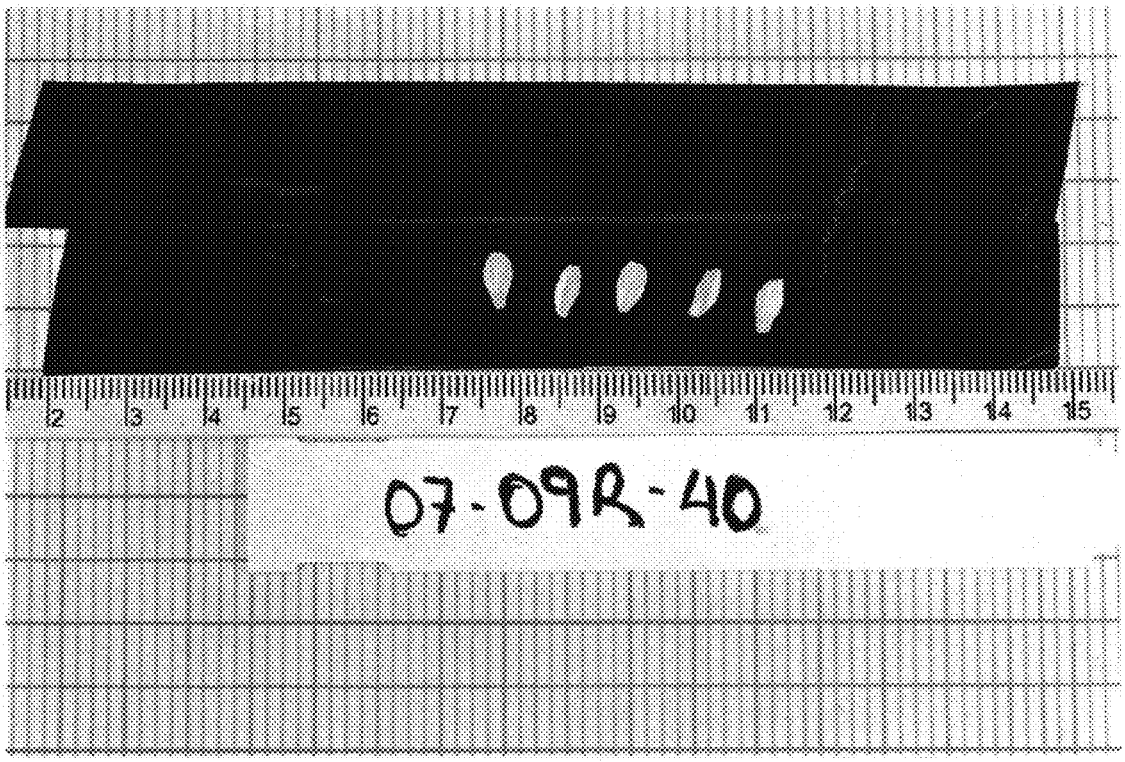
FIG. 10 shows typical petals of the new variety (designated 07.09R.40) with narrow elliptic shape and RHS white group color (near 155 B).
Figure 11:
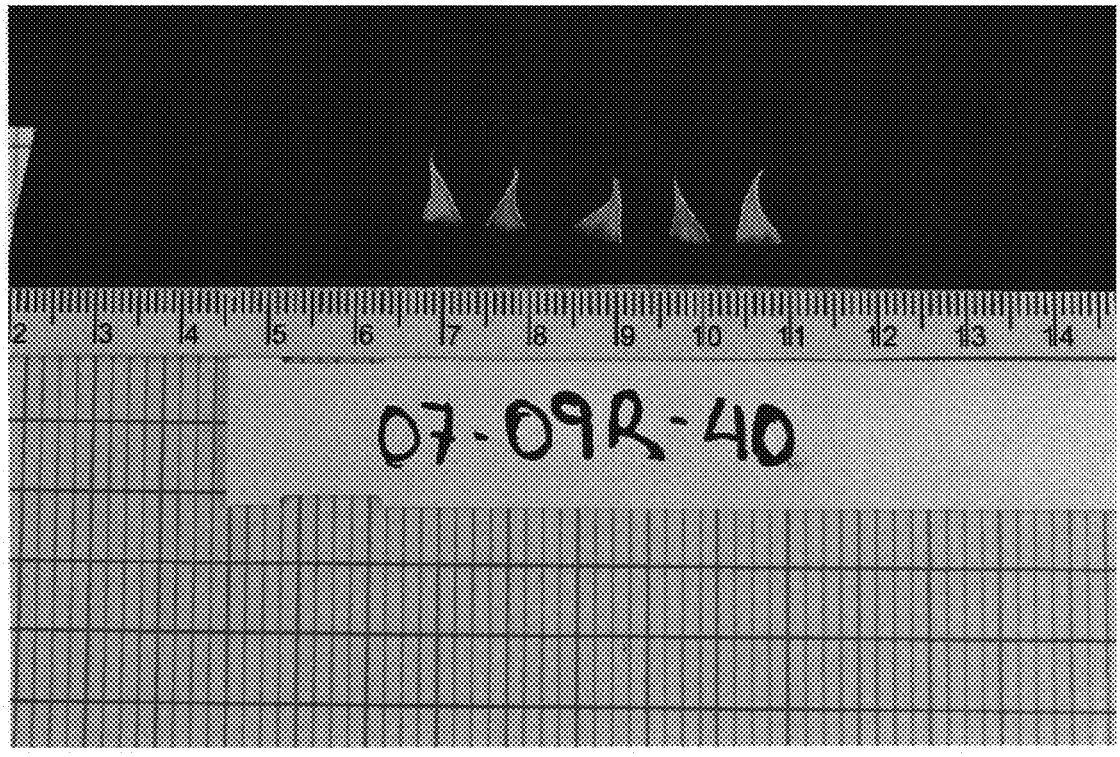
FIG. 11 shows typical lower surfaces of the sepals of the new variety (designated 07.09R.40) with triangular shape, acuminate apex and RHS green group color (near 143 C to 143 B).
Figure 12:
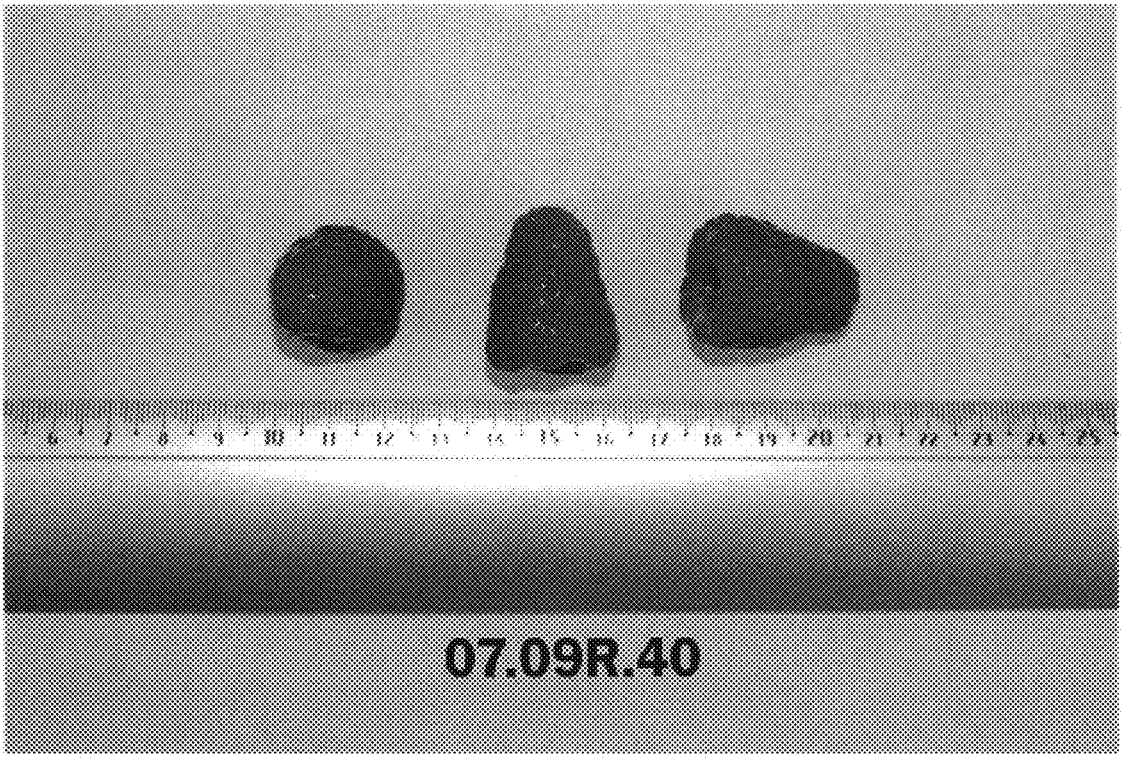
FIG. 12 and FIG. 13 show typical fruits of the new variety (designated 07.09R.40) with conical shape in lateral view and red color (RHS red group near 42 B to 42 A).
Figure 13:
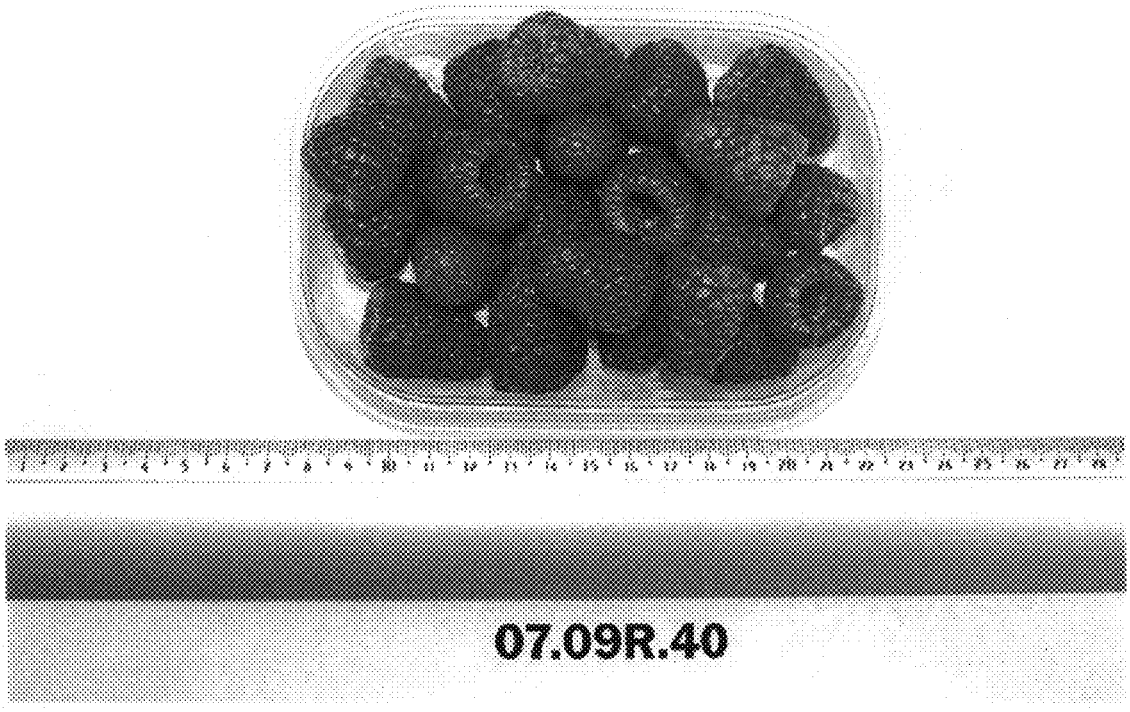
Figure 14:
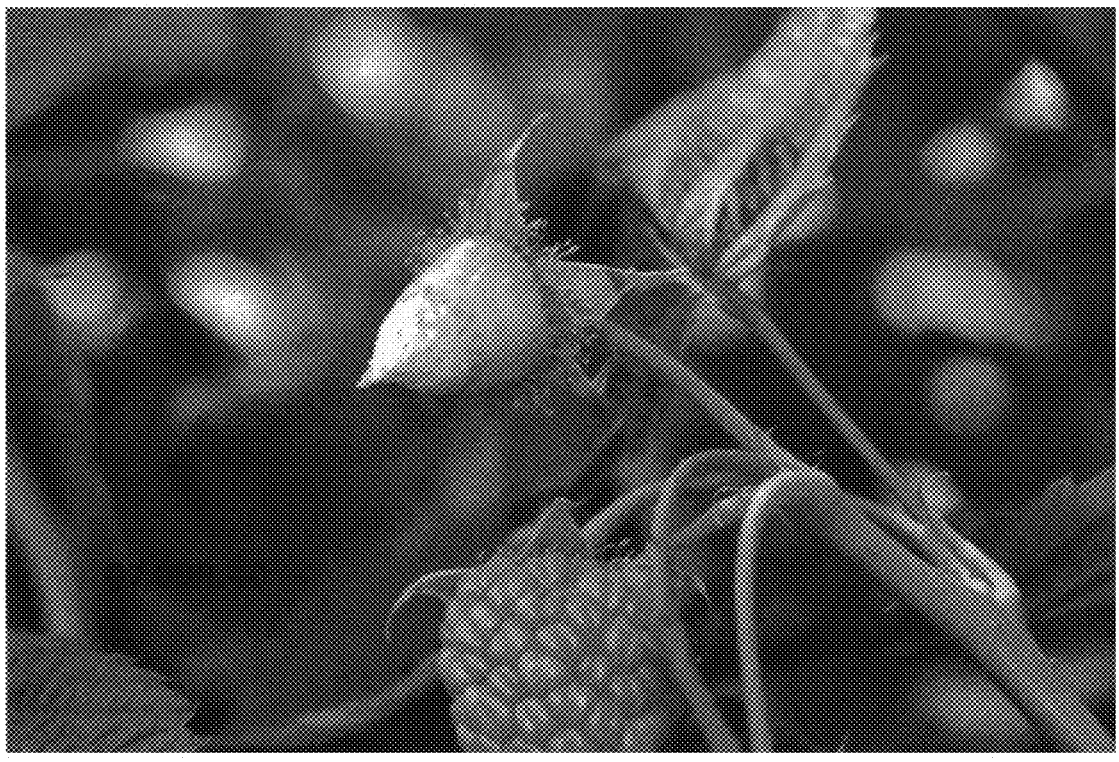
FIG. 14 shows typical receptacle of the new variety (designated 07.09R.40) with conical shape and yellow-white color (RHS yellow-white group near 158 C to 158 B).
Figure 15:
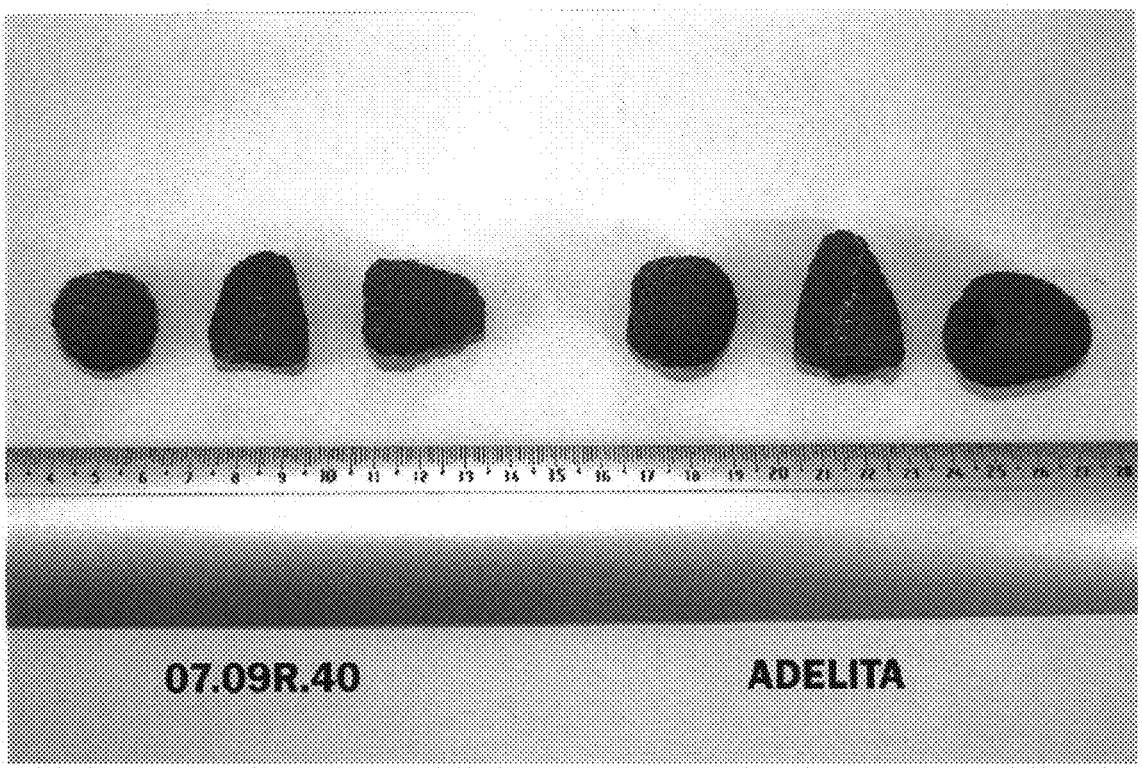
Figure 16:
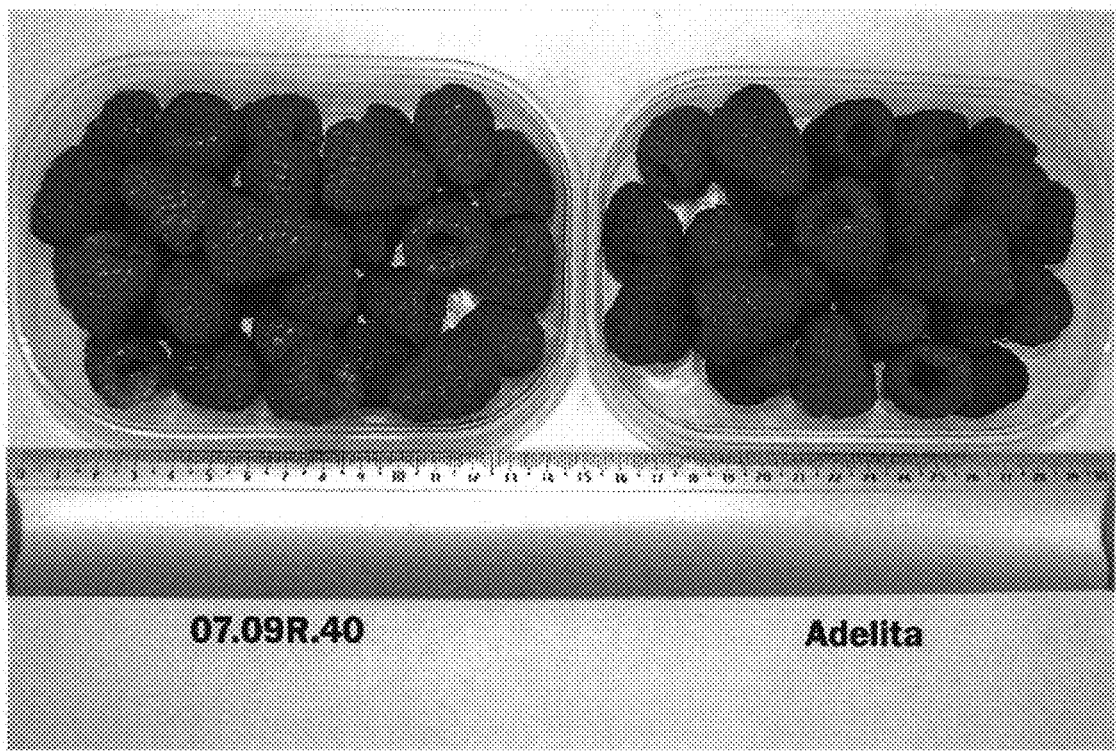

FIG. 15 and FIG. 16 show the fruit of raspberry variety 'Adelita' (U.S. Plant Pat. No. 25,245) which shows a red color fruit (RHS red group near 47 A to 46 A) in comparison with the fruit of the new variety (designated 07.09R.40) which shows a fruit red color fruit (RHS red group near 42 B to 42 A).

Figure 17:
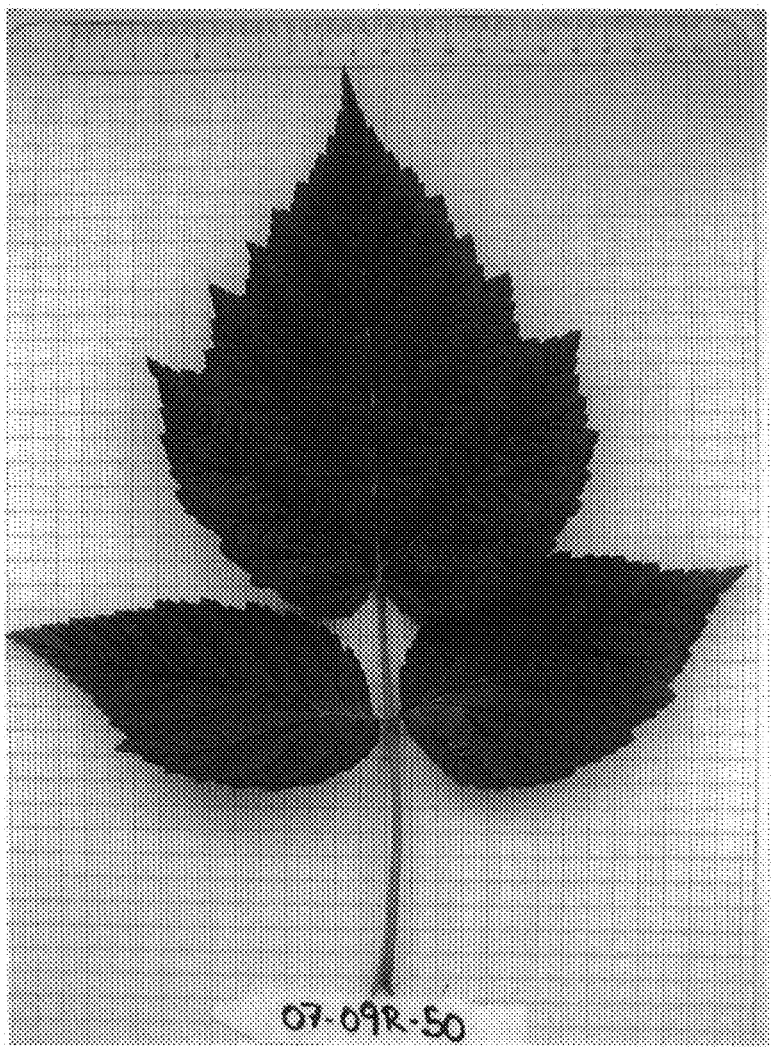

FIG. 17 shows the upperside of a complete leaf of raspberry variety 'Adelita' (U.S. Plant Pat. No. 25,245) (designated 07.09R.50). It can be seen that the leaf color of the upperside of raspberry variety 'Adelita' (U.S. Plant Pat. No. 25,245) (designated 07.09R.50) is a green color (RHS green group near 138 A to 137A), and the length of the terminal leaflet in raspberry variety 'Adelita' (U.S. Plant Pat. No. 25,245) (designated 07.09R.50) is long to very long.

Figure 18:
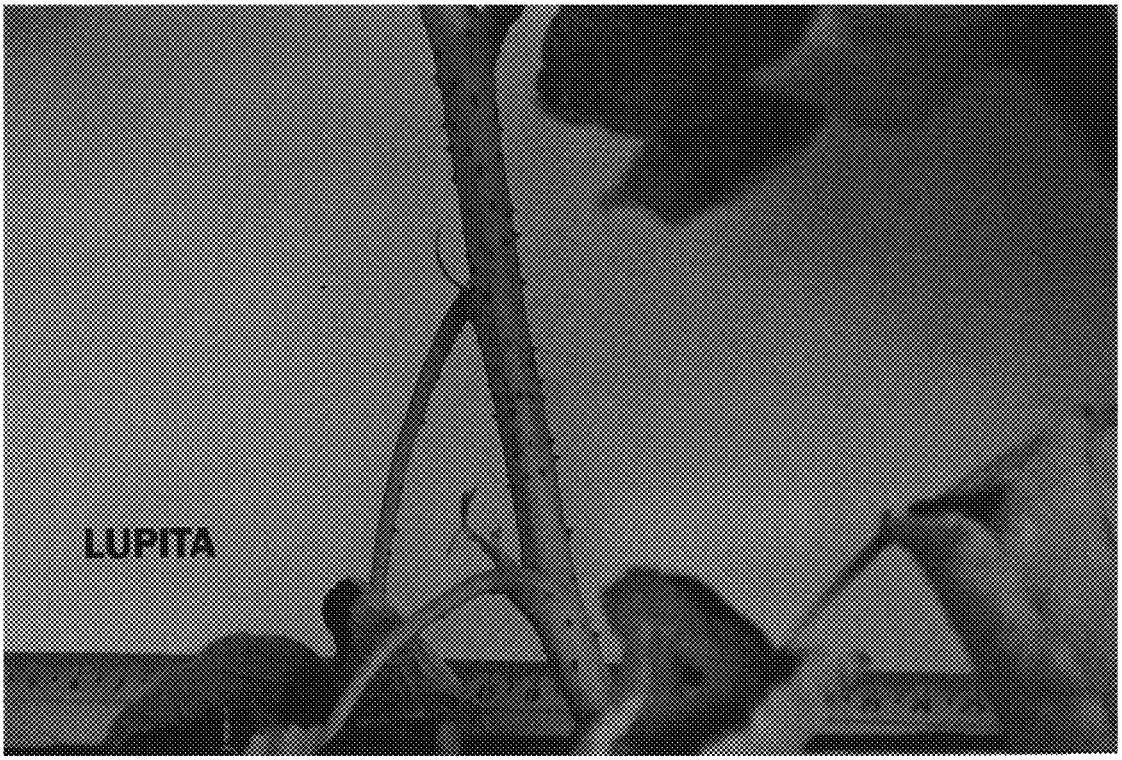

FIG. 18 shows the cane of raspberry variety 'Lupita' (U.S. Plant Pat. No. 25,171) with a medium density of spines.

Figure 19:
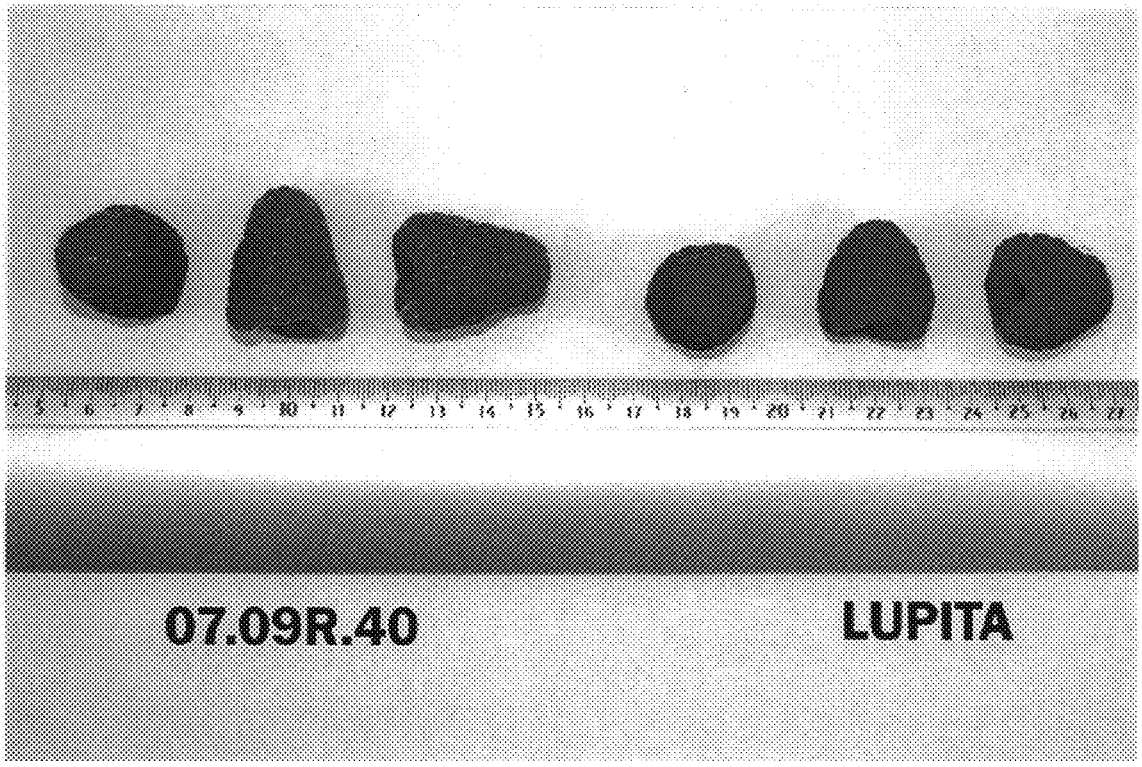
Figure 20:
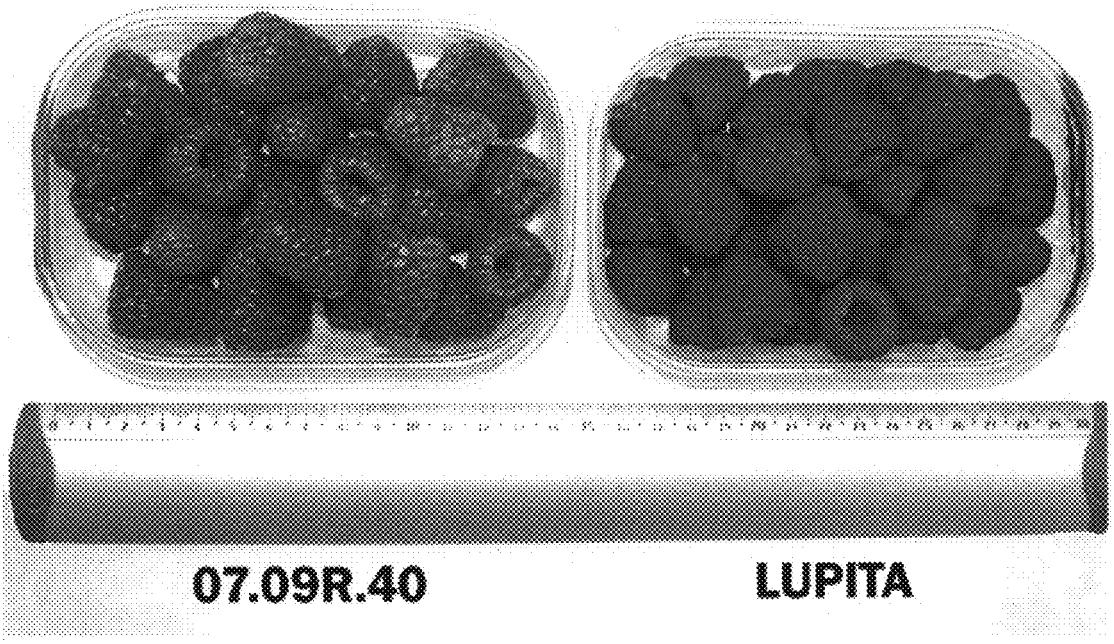

FIG. 19 and FIG. 20 show the fruit of raspberry variety 'Lupita' (U.S. Plant Pat. No. 25,171) which shows a red color fruit (RHS red group near 45 D to 46 B), in comparison with the fruit of the new variety (designated 07.09R.40) which shows a fruit red color fruit (RHS red group near 42 B to 42 A).

DESCRIPTION OF THE NEW VARIETY

The following description is in accordance with UPOV terminology and the color terminology herein is in accordance with The Royal Horticultural Society Colour Chart (R.H.S.C.C.), 3rd edition published in 1995.

The color descriptions and other phenotypical descriptions may deviate from the stated values and descriptions depending upon variation in environmental, seasonal, climatic and cultural conditions.

Throughout this specification, color names beginning with a small letter signify that the name of that color, as used in common speech is aptly descriptive. Color names beginning with capital letter designate values based upon The R.H.S. Colour Chart published by The Royal Horticultural Society, London, England, 1995.

The following detailed description of the new variety is based upon observations taken of plants and fruits grown "underglass", i.e., under tunnel, in the farm of La Mogalla in Cartaya (Huelva), Spain, 7° W., 37° N., 45 feet elevation.

PROPAGATION

The new variety is principally propagated by way of root cuttings. Although propagation by root cuttings is presently preferred, other know methods of propagating raspberry plants may be used. Raspberries root and develop well after transplanting.

'Plapink 0740' is propagated by root cuttings. It is a primocane variety with fruit production from middle October through the end of January on primocanes and in the ensuing year from the middle of April and ending in May. 'Plapink 0740' is a self-fertile variety. It produces large quantities of pollen throughout the seasons and pollination is good.

Trials were pursued in in Cartaya (Huelva), Spain, about 7° W, 37° N. 45 feet elevation (15 meters high). The plants described are from high elevation nursery in Segovia, Spain, 3° 59'W., 41° 22'N., 2742 feet elevation. Plants were planted on June 25 in the first year and June 28 in the second year with a sample size of three repetitions every year and 120 plants per repetition every year. The growing period in Huelva, Spain, where the observations on primocane production were made, is between the end of June and the end of May of the following year. 'Plapink 0740' is a primocane variety, with consistent fruit production beginning in middle October and ending in January on primocanes and in the ensuing year beginning in middle April and ending in May. After planting as aforesaid, plants are grown in raised beds under tunnel. Water and fertilizer were applied through drip irrigation.

GENERAL

TABLE 1

Table 1 shows the accumulated production of 1st Quality Fruit (g/plant) of the new variety 'Plapink 0740' when compared to its closest varieties 'Adelita' and 'Lupita'.

| Variety | Middle in October and ending in January | Middle in April and ending in May | Total |
|---|---|---|---|
| Plapink 0740 | 310.43 | 216.37 | 526.80 |
| ADELITA | 948.71 | 760.31 | 1709.02 |
| LUPITA | 287.32 | 445.62 | 732.94 |

TABLE 2

Table 2 shows the Accumulated Total Yield of 1st and 2nd quality fruit (g/plant) of the new variety 'Plapink 0740' when compared to its closest varieties 'Adelita' and 'Lupita'.

| Variety | 1st + 2nd Quality Middle in October and ending in January | 1st + 2nd Quality Middle in April and ending in May | Total |
|---|---|---|---|
| Plapink 0740 | 468.64 | 226.22 | 694.86 |
| ADELITA | 1208.28 | 899.81 | 2108.09 |
| LUPITA | 372.23 | 508.50 | 880.73 |

TABLE 3

Table 3 shows the Production beginning in middle October and ending in January of First Quality Fruit (1st quality) and Second Quality Fruit (2nd quality) in g/plant, of the new variety 'Plapink 0740' when compared to its closest varieties 'Adelita' and 'Lupita'

| Variety | 1st Quality | 2nd Quality | TOTAL (1st Quality + 2nd Quality) | % 2nd Quality |
|---|---|---|---|---|
| Plapink 0740 | 310.43 | 158.21 | 468.64 | 33.76 |
| ADELITA | 948.71 | 259.57 | 1208.28 | 21.48 |
| LUPITA | 287.32 | 84.91 | 372.23 | 22.81 |

% 2nd Quality = (2nd Quality/TOTAL) × 100

TABLE 4

Table 4 shows production beginning in middle April and ending in May of First Quality Fruit (1st quality) and Second Quality Fruit (2nd quality) in g/plant, of the new variety 'Plapink 0740' when compared to its closest varieties 'Adelita' and 'Lupita'.

| Variety | 1st Quality | 2nd Quality | TOTAL (1st Quality + 2nd Quality) | % 2nd Quality |
|---|---|---|---|---|
| Plapink 0740 | 216.37 | 9.85 | 226.22 | 4.35 |
| ADELITA | 760.31 | 139.50 | 899.81 | 15.50 |
| LUPITA | 445.62 | 62.88 | 508.50 | 12.36 |

% 2nd Quality = (2nd Quality/TOTAL) × 100

TABLE 5

Table 5 shows the weight (g/Fruit) in two production periods: October to January/April to May of the new variety 'Plapink 0740' when compared to its closest varieties 'Adelita' and 'Lupita'.

| Variety | Middle October to end January | Middle April to end May |
|---|---|---|
| Plapink 0740 | 7.3-6.5 | 6.0-4.6 |
| ADELITA | 8.1-6.9 | 6.3-5.1 |
| LUPITA | 7.0-6.1 | 5.4-5.3 |

WEIGHT is shown as the average weight per fruit (g/fruit) in First Quality Fruits.

DETAILED DESCRIPTION OF THE NEW VARIETY

The following additional information is provided to further describe the new variety:

Variety: 'Plapink 0740'.

Breeder Ref: 07.09R.40 .

Classification: *Rubus idaeus* L.

Plants were grown in containers of 48 liters of capacity and are described during cultivar's primocane.

Plant:

- *Growth habit*.—Semi-Upright.
- *Vigor*.—Medium.
- *Cold tolerance*.—The new variety has not been grown in harsh winter conditions. It is expected to be of medium tolerance.
- *Heat tolerance*.—The new variety has not been grown in harsh summer conditions. It is expected to be of medium tolerance.

Cultivar's primocane cane:

- *Length*.—About 150 cm to 165 cm.
- *Diameter*.—About 1.3 cm to 1.5 cm.
- *Texture*.—Smooth.
- *Internode length*.—About 4.5 to 4.8 cm.
- *Pubescence*.—Absent.
- *Anthocyanin coloration of apex during rapid grow period*.—Absent.
- *Cane color*.—RHS yellow green group (near 144 C to 144 B).

Spines:

- *Shape*.—Conical.
- *Density*.—Sparse to medium.
- *Number/cm*.—About 2 to 3.
- *Length*.—About 0.07 cm to 0.11 cm.
- *Width*.—About 0.08 cm to 0.10 cm at the base.
- *Apex*.—Straight.
- *Color*.—RHS greyed red group color (near 180 B to 180 A).
- *Texture*.—Rigid.

Leaf:

- *Type*.—Compound.
- *Number of leaflets*.—3.
- *Arrangement of lateral leaflets*.—Touching.
- *Overlapping of lateral leaflets with terminal leaflet*.—Free.
- *Upperside*.—RHS green group color (near 139 C to 139 B).
- *Underside*.—RHS green group color (near 133 C to 133 B).
- *Length*.—About 17.5 cm to 18.5 cm.
- *Width*.—About 15.5 cm to 16.5 cm.
- *Profile of leaflets in cross section*.—Straight.
- *Relief between veins*.—Medium to strong.

Lateral leaflet:

- *Shape*.—Elliptic.
- *Length*.—About 7.0 cm to 8.0 cm.
- *Width*.—About 3.5 cm to 4.0 cm.
- *Shape of tip*.—Acuminate.
- *Shape of base*.—Acute.
- *Shape of margin*.—Serrate.
- *Upperside rugosity*.—Medium to strong.
- *Underside texture*.—Smooth.
- *Upperside texture*.—Smooth.
- *Upperside coloration*.—RHS green group color (near 139 C to 139 B).
- *Underside coloration*.—RHS green group color (near 133 C to 133 B).
- *Venation pattern*.—Reticulate or penniveined.
- *Upperside venation coloration*.—RHS yellow green group color (near 144 B to 144 A).
- *Underside venation coloration*.—RHS yellow green group color (near 144 B to 144 A).

Terminal leaflet:

- *Length/width ratio*.—Longer than broad.
- *Length*.—About 10 cm.
- *Width*.—About 6.0 cm to 6.5 cm.
- *Cross section*.—Concave.
- *Upperside*.—RHS green group color (near 139 C to 139 B).
- *Underside*.—RHS green group color (near 133 C to 133 B).
- *Shape of leaflet*.—Ovate.
- *Shape of tip*.—Acuminate.
- *Shape of base*.—Rounded.
- *Shape of margin*.—Serrate.
- *Upperside rugosity*.—Medium to strong.
- *Underside texture*.—Smooth.
- *Upperside texture*.—Smooth.

*Venation pattern*.—Reticulate or penniveined.
*Upperside venation coloration*.—RHS yellow green group color (near 144 B to 144 A).
*Underside venation coloration*.—RHS yellow green group color (near 144 B to 144 A).

Rachis:
*Length between the terminal leaflet and adjacent lateral leaflet*.—About 2.5 cm to 3.0 cm.
*Coloration*.—RHS yellow green group color (near 144 B to 144 A).

Petiole:
*Color*.—RHS yellow green group color (near 144 B to 144 A).
*Length*.—About 4.0 cm to 4.5 cm.
*Length* (*rachis with petiolule*).—About 6.5 cm to 7.5 cm.
*Diameter*.—About 3.0 mm to 3.5 mm in the Petiolule and about 1.5 mm to 2.0 mm in the rachis.
*Spines*.—Absent or very few.
*Petiole texture*.—Smooth.

Stipule:
*Quantity per leaf*.—2.
*Shape*.—Erect.
*Length*.—About 7.0 mm to 9.0 mm.
*Width*.—Very narrow. About 0.2 mm to 0.3 mm.
*Color* (*both surfaces*).—RHS yellow green group color (near 144 C to 144 B).

Flower bud:
*Shape*.—Trapezoidal.
*Diameter*.—About 7.0 mm to 9.0 mm.
*Length*.—About 10.0 mm to 11.0 mm.
*Color*.—RHS green group (near 143 C) trough RHS yellow green group (near 144 A).

Pedicel:
*Length*.—About 3.0 cm to 3.5 cm.
*Diameter*.—About 1.9 mm to 2.5 mm.
*Pedicel color*.—RHS yellow green group color (near 144 B to 144 A).
*Surface texture*.—Smooth.
*Density of spines*.—Sparse.

Flower:
*Diameter*.—About 1.9 cm to 2.1 cm.
*Number of pistils per flower*.—About 95 to 120.
*Pistil length*.—About 3.0 mm to 4.0 mm.
*Ovary shape*.—Pyriform.
*Ovary length*.—Medium.
*Ovary width*.—Narrow.
*Ovary color*.—RHS green group color (near 142 C to 142 B).
*Style length*.—About 0.15 cm to 0.20 cm.
*Style color*.—RHS white group color (near 155 C).
*Number of stamens per flower*.—About 110 to 125.
*Stamen length*.—About 0.4 cm to 0.5 cm.
*Stamen shape*.—Cylindrical lengthened.
*Stamen color*.—RHS green group color (near 142 D).
*Pollen*.—Amount: Moderate to abundant.
*Pollen color*.—RHS yellow green group color (near 153 C to 153 B).

Petal:
*Number of petals per flower*.—About 5 to 6.
*Shape*.—Narrow elliptique.
*Length*.—About 7.0 mm to 8.0 mm.
*Width*.—About 3.0 mm to 4.0 mm.
*Apex shape*.—Flat rounded.
*Base shape*.—Narrow.
*Margin*.—Smooth and regular.
*Texture*.—Smooth.
*Color* (*both surfaces*).—RHS white group color (near 155 B).

Peduncles:
*Length*.—About 18.0 cm to 20.0 cm.
*Diameter*.—About 4.0 mm to 5.0 mm.
*Surface texture*.—Smooth.
*Density of spines*.—Sparse to medium.
*Color*.—RHS yellow-green group (near 144 B to 144 A).
*Presence or absence of anthocyanin*.—Absent.

Receptacle:
*Length*.—About 1.5 cm to 1.9 cm.
*Diameter*.—About 0.8 cm to 1.0 cm.
*Shape*.—Conical.
*Color*.—RHS yellow-white group (near 158 C to 158 B).

Sepal:
*Number of sepals per flower*.—About 5 to 6.
*Shape*.—Triangular.
*Length*.—About 7.0 mm to 9.0 mm.
*Width*.—About 4.0 mm to 5.0 mm.
*Apex shape*.—Acuminate.
*Base shape*.—Large at the base forming the calyx.
*Margin*.—Smooth and regular.
*Texture of upper and lower surface*.—Smooth.
*Color*.—RHS green group color (near 143 C to 143 B).

Fruit:
*Shape*.—Conical.
*Length*.—About 2.3 cm to 2.5 cm.
*Width*.—About 2.1 cm to 2.3 cm.
*Color*.—RHS red group color (near 42 B to 42 A).
*Number of drupelets per fruit*.—About 90 to 110.
*Size of single drupelet*.—About 0.30 cm to 0.35 cm.
*Drupelet arrangement around the berry*.—Slightly irregular.
*Glossiness*.—Strong.
*Firmness*.—Firm.
*Adherence to plug*.—Medium.
*Diameter hollow center*.—About 0.9 cm to 1.1 cm.

Seed:
*Number of seeds per drupelet*.—1.
*Shape*.—Slightly reniform.
*Color*.—RHS greyed-orange group (near 164 D to 165 D).
*Surface texture*.—Wrinkled.

Fruiting lateral cane:
*Number of fruit per fruiting lateral cane*.—About 8 to 12 fruits.
*Average number of fruit per node*.—3 to 4 fruits.

Length of fruiting period on current year's cane:
*Autumn*.—From middle of October to end of January.
*Spring*.—From middle of April to end of May.

Number of current season's cane:
*Production in autumn*.—Medium.
*Production in spring*.—Many.

Characteristics of production from middle April through ending May:
*Cane's length*.—About 140 cm to 150 cm.
*Cane's diameter*.—About 1.3 to 1.5 cm.
*Texture*.—Smooth.
*Internode length*.—About 4.0 to 4.5 cm.
*Pubescence*.—Absent.

*Anthocyanin coloration of apex during rapid grow period*.—Absent.

*Cane color*.—RHS yellow green group (near 144 C to 144 B).

*Fruiting lateral cane's length*.—About 70 to 80 cm.

*Fruiting lateral cane's attitude*.—Semi-upright.

*Number of fruit per fruiting lateral cane*.—About 8 to 12 fruits.

*Average number of fruit per node*.—About 3 to 4 fruits.

*Spine's shape*.—Conical.

*Spine's density*.—Medium.

*Spine's number/cm*.—About 2 to 3.

*Spine's length*.—About 0.07 to 0.11 cm.

*Spine's width*.—About 0.08 to 0.10 cm at the base.

*Spine's apex*.—Straight.

*Spine's color*.—RHS greyed red group color (near 180 B to 180 A).

*Spine's texture*.—Rigid.

*Time of vegetative bud burst*.—About middle February.

*Time of flowering data*.—10% flowering occurs about the end of March.

*First mature fruits* (15-20 *g/plant*).—About middle of April.

*Fruiting period*.—From middle of April through end of May.

Disease resistance: No particular sensitivity to any disease or pest has been observed for 'Plapink 0740'.

Use/market: The berries of 'Plapink 0740' are suitable for consumption as fresh fruit. Also, they are amenable to processing.

Fruit bearing type: Both on previous year's cane in autumn and current year's cane in spring.

Storage qualities: 'Plapink 0740' fruit maintain their quality characteristics when keeping them in a frigo chamber at temperatures of about 2° C. during 48 hours. The fruit's color remains substantially the same. Shelf life of 'Plapink 0740' is good.

Planting date: Each year about June 25 in the farm of La Mogalla, in Cartaya (Huelva), Spain, about 7° W, 37° N, 45 feet elevation.

Time of flowering: 10% Flowering on primocane occurs each year about October 2.

First mature fruits: Each year about October 26 (15-20 g/plant), with a maximum production at the beginning of December.

I claim:

1. A new and distinct raspberry plant of the variety substantially as shown and described.

* * * * *